US005321971A

United States Patent [19]

Hobbs et al.

[11] Patent Number: 5,321,971

[45] Date of Patent: Jun. 21, 1994

[54] GAS DIFFUSION CONTROL ASSEMBLY

[75] Inventors: Bryan S. Hobbs, Chertsey; Yat S. Chan, London, both of England

[73] Assignee: The Governor and Company of the Bank of Scotland, Edinburgh, Scotland

[21] Appl. No.: 974,383

[22] Filed: Nov. 10, 1992

Related U.S. Application Data

[63] Continuation of Ser. No. 783,625, Oct. 24, 1991, abandoned.

[30] Foreign Application Priority Data

Nov. 12, 1990 [GB] United Kingdom ................. 9024521
Mar. 27, 1991 [GB] United Kingdom ................. 9106531

[51] Int. Cl.5 ................ G01N 31/00
[52] U.S. Cl. ................ 73/23.2; 73/31.05
[58] Field of Search ................ 73/23.2, 31.05

[56] References Cited

U.S. PATENT DOCUMENTS

| | | | |
|---|---|---|---|
| 3,361,162 | 1/1968 | Prestridge et al. | 251/205 |
| 3,840,209 | 10/1974 | James | 251/216 |
| 3,924,219 | 12/1975 | Braun | 73/31.05 |
| 4,326,200 | 5/1982 | Bushman | 73/31.05 |
| 4,406,770 | 9/1983 | Chan et al. | 204/431 |
| 4,446,000 | 5/1984 | Cullinane, Jr. | 204/431 |
| 4,474,648 | 10/1984 | Tantram et al. | 204/431 |
| 4,587,003 | 5/1986 | Tantram et al. | 204/431 |
| 4,633,704 | 1/1987 | Tantram et al. | 73/31.05 |
| 4,824,551 | 4/1989 | Rupich | 204/431 |
| 4,986,502 | 1/1991 | Ceroke | 251/216 |
| 5,082,239 | 1/1992 | Field | 251/205 |

FOREIGN PATENT DOCUMENTS

| | | | |
|---|---|---|---|
| 0307790 | 3/1989 | European Pat. Off. . | |
| 0068494 | 6/1977 | Japan | 422/98 |
| 0117162 | 9/1981 | Japan | 73/31.05 |
| 3081658 | 5/1991 | Japan | 73/31.05 |
| 1571282 | 7/1980 | United Kingdom . | |
| 2049952 | 12/1980 | United Kingdom . | |
| 2169714 | 7/1986 | United Kingdom | 73/31.05 |
| 2169715 | 7/1986 | United Kingdom | 73/31.05 |
| 2175094 | 11/1986 | United Kingdom | 73/31.05 |

*Primary Examiner*—Michael J. Tokar
*Assistant Examiner*—Raymond Y. Mah
*Attorney, Agent, or Firm*—Lee, Mann, Smith, McWilliams, Sweeney & Ohlson

[57] ABSTRACT

A gas diffusion control assembly comprises a gas inlet; a restriction to the rate of flow of gas or vapor from the gas inlet in the form of a porous diffusion barrier extending across the gas inlet; and a polythene disc for causing all gas or vapor passing out of the inlet into the diffusion barrier to diffuse through part of the barrier along a path with a lateral outward component relative to the direction of action through the gas inlet.

7 Claims, 4 Drawing Sheets

2
1
3
6
7
4

2
31
10
30
1
SA1
3
4
5
6
14
SA2
11
13
12
17
SA3
18
15
16

GAS DIFFUSION CONTROL ASSEMBLY

This application is a continuation of application Ser. No. 783,625, filed Oct. 24, 1991, now abandoned.

FIELD OF THE INVENTION

This invention relates to a gas diffusion control assembly, for example for use with a gas sensor, and a method of making such an assembly.

DESCRIPTION OF THE PRIOR ART

An example of a gas sensor is an electro-chemical sensor for the measurement of concentrations of gas or vapor in accordance with the limiting current principle comprising an electrolytic cell having a sensing electrode, a counter electrode and an intervening body of electrolyte, the sensor also including a restriction to the rate of access of gas or vapor to the sensing electrode. Electro-chemical sensors of this type are described in GB-A-1571282 and GB-A-2049952. Commercial oxygen sensors which have been built incorporate a capillary to constitute the barrier. Although these sensors have proved to be very successful, they are relatively expensive to build and, particularly in the case of oxygen sensors, have a relatively short service period. This is because high concentrations of oxygen will cause the generation of relatively high currents which cause the metallic counter electrode relatively rapidly to be consumed. It is also necessary in commercial sensors to provide some form of bulk flow limiting means, for example a low permeability, but high diffusibility, microporous capping membrane over the capillary to the capillary to minimize transient effects caused by sudden pressure changes, draughts and flexure of the electrodes in changing orientation of the sensor.

The need to achieve longer service life calls for more restrictive diffusion barriers; smaller diameter capillaries become increasingly difficult and more expensive to fabricate and suffer greater bulk flow effects. There is a need therefore to devise alternative barrier designs to overcome the limitations of conventional capillary barriers.

SUMMARY OF THE INVENTION

In accordance with one aspect of the present invention, a gas diffusion control assembly comprises a gas inlet; a restriction to the rate of flow of gas or vapor from the gas inlet in the form of a porous diffusion barrier extending across the gas inlet; and control means for causing all gas or vapor passing out of the inlet into the diffusion barrier to diffuse through part of the barrier along a path with a lateral outward component relative to the direction of access through the gas inlet.

The porous barrier may comprise a gas phase diffusion barrier in which gas remains in the gas phase during its passage through the barrier, a Knudsen barrier in which the active pores are sufficiently small as to cause diffusion through them to be in accordance with the Knudsen principle (ie. diffusion rate governed by pore wall collisions, rather than inter-molecular collisions), or a mixture of the two types of barrier.

The control means for causing lateral gas diffusion may comprise an impermeable member such as a polythene disk bonded to the barrier.

Preferably, the assembly is formed substantially symmetrically, the gas inlet defining a gas diffusion path centered on the axis of symmetry. In this case, the means for causing lateral gas diffusion is arranged preferably to cause gas to diffuse laterally outward substantially symmetrically about the axis of symmetry.

When the assembly is incorporated into a gas sensor having a sensing electrode with a microporous backing tape, the sensing electrode is preferably positioned parallel with respect to the porous diffusion barrier such that gas can enter the microporous backing tape of the electrode beyond the periphery of the area defined by the control means (such as an impermeable polythene disc), and thence into an electrocatalyst layer of the sensor without any further significant diffusion resistance.

Orientation effects in conventional sensors can be caused by the flexure of the sensing electrode which leads to bulk flow of gas and resultant current transients on the sensor signal. The magnitude of these transients is related to the internal gas volume downstream of the diffusion barrier. The above barrier design reduces any bulk flow effects, including orientation effects, by presenting a low permeability gas access pathway.

In accordance with a second aspect of the present invention a gas sensor comprises a sensing electrode catalyst layer; a counter electrode; and a gas diffusion control assembly according to the first aspect of the invention, in which the porous diffusion barrier is fixed directly to the sensing electrode catalyst layer. This fixing may be by direct pressure bonding, heat sealing, or any other means between the barrier and electrode. In one embodiment the porous barrier and control means, eg. an impermeable disc composite, act as both the main diffusion barrier and the electrode supporting tape, thereby reducing the internal gas volume to a very low level and virtually eliminating orientation effects due to electrode flexure.

In accordance with a third aspect of the present invention, a gas diffusion control assembly comprises a gas inlet; a restriction to the rate of access of gas or vapor to the gas inlet in the form of a gas phase diffusion barrier extending across the gas inlet; and control means for causing all gas or vapor to pass to the gas inlet through part of the barrier along a path with a lateral component relative to the direction of access through the gas inlet.

Once again, the control means for causing lateral gas diffusion may comprise an impermeable member such as a polythene disc bonded to the barrier.

The assembly according to the third aspect of the present invention is particularly useful since by providing the barrier upstream of the gas inlet, it is possible to control accurately the diffusibility of the barrier and, in the case of a gas sensor to which the assembly is connected, tune the sensor signal.

Thus, in accordance with a fourth aspect of the present invention, a method of manufacturing a gas diffusion control assembly comprises providing a gas inlet through which gas or vapor can travel; positioning a porous diffusion barrier across the gas inlet to restrict the rate of access of gas or vapor to the gas inlet; positioning a thermoplastic member in contact with the porous diffusion barrier; and heating the thermoplastic member and the porous diffusion barrier so as to cause the thermoplastic material to impregnate the barrier and/or to cause the pores of the barrier to be compressed until a desired diffusibility is achieved.

This tuning operation is not easily achieved with existing assemblies (which make use of Knudsen barriers) since these assemblies have a metal covering over the barrier. This metal covering or cap compresses the barrier so that the pores are reduced to Knudsen dimensions. In contrast, the fourth aspect of the invention recognizes that by exposing the porous diffusion barrier, it is possible to control the diffusion characteristic of the barrier by a suitable heat treatment.

It should be noted that the porous diffusion barrier used in methods according to the fourth aspect of the invention may comprise a gas phase diffusion barrier, a Knudsen diffusion barrier or a mixture of the two types of barrier.

In one application, the gas diffusion control assembly is connected to a gas sensing device to form a gas sensor, the assembly controlling the rate of access of gas or vapor to the sensing device. For example, the gas sensing device may comprise an electrochemical sensor for the measurement of concentrations of gas or vapor in accordance with the limiting current principle, the sensing device comprising an electrolytic cell having a sensing electrode, a counter electrode and an intervening body of electrolyte.

The gas sensor is much simpler and cheaper to construct and generates currents which are reduced compared to equivalent capillary based sensors. For example, in the case of an oxygen sensor, a conventional capillary sensor will generate a current in the order of one mA in air (21% oxygen) whereas a sensor according to the invention can easily be constructed which generates much smaller currents in the order of 0.1 mA or less in ambient air. Furthermore, the problems of bulk flow are considerably reduced and the capillary is dispensed with. This leads to a much cheaper and compact construction.

In accordance with a fifth aspect of the present invention, a gas sensor comprises:

a first sub-assembly including a gas sensing device having a sensing electrode; a gas inlet forming part of a gas path to the sensing device; a restriction to the rate of access of gas or vapor to the gas sensing device in the form of a porous diffusion barrier; and means for causing all gas or vapor to diffuse through part of the barrier along a path with a lateral component relative to the direction of gas access through the gas inlet;

a second sub-assembly including a counter electrode; and, a third sub-assembly to which the first and second sub-assemblies are mounted, the third sub-assembly including electrical contacts connected to the sensing and counter electrodes respectively.

Preferably, the first sub-assembly comprises a gas diffusion control assembly according to the first or third aspect of the invention or manufactured in accordance with the fourth aspect of the invention.

Typically, in all aspects of the invention, the porous diffusion barrier will have a generally disc like form but in some cases it may be in the form of a strip or sector such as a semi-circle or quadrant.

DETAILED BRIEF DESCRIPTION OF THE DRAWINGS

Some examples of electro-chemical gas sensors according to the invention will now be described with reference to the accompanying drawings, in which.

BRIEF DESCRIPTION OF THE EMBODIMENTS

Figure 1:
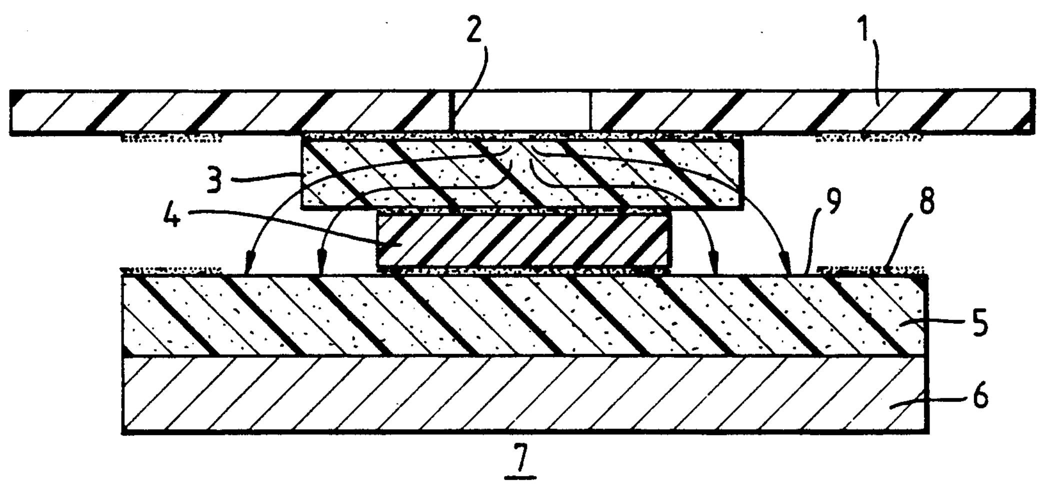
FIG. 1 is a partially exploded longitudinal section through part of a first example.
Figure 6:
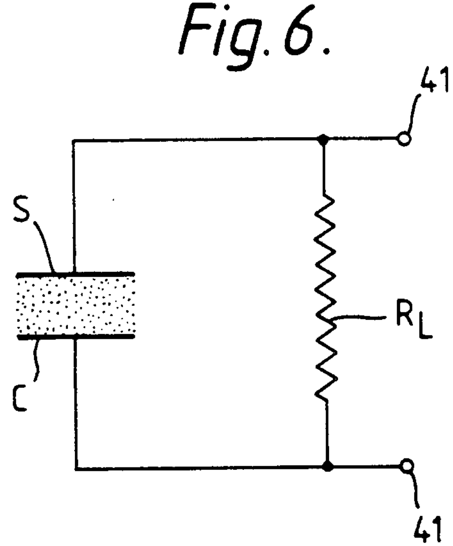
FIG. 6 illustrates a simple circuit to which a two electrode gas sensor is connected.

The sensor of which part is shown in FIG. 1 includes a circular top plate 1 (of diameter about 30 mm) provided with a gas access hole 2 having a length of about 3 mm and a diameter of about 2 mm. Heat sealed to the plate 1 is a porous PTFE disk 3 of diameter about 10 mm and thickness about 0.18 mm which defines a diffusion barrier. The diffusion barrier may be a pure gas phase diffusion barrier, a barrier operating on the Knudsen principle, or a barrier with a combination of these properties. Gas enters the sensor through the access hole 2 and passes into the diffusion barrier 3. The gas is prevented from passing directly, in a straight line, through the barrier 3 by a polythene disk 4 (diameter 7 mm and thickness 0.1 mm) heat sealed to the underside of the barrier 3. A porous PTFE backing tape 5 (19 mm diameter and 0.18 mm thickness) is heat sealed to the disk 4 while a sensing electrode catalyst layer 6 (19 mm diameter and 0.18 mm thickness) is mounted to the tape 5. Electrolyte contacts the catalyst layer 6 in the region 7. An annular portion of the surface of the backing tape 5 is heat sealed at 8 to the top plate 1 (shown spaced apart in FIG. 1) to prevent electrolyte reaching the barrier 3. The sensor would also include a metallic counter electrode, an intervening body of electrolyte absorbed in separators between the electrodes, and suitable containment hardware which are not shown in this drawing. The sensor is connected in a conventional electric circuit of the type shown in FIG. 6. In this circuit, the sensing electrode 6 (indicated by S) and the counter electrode C are connected across a load resistor $R_L$. Electrochemical reactions at the electrodes generate an electric current which flows between the electrodes through the circuit containing $R_L$. The current generated by this sensor design is directly proportional to the oxygen concentration in the atmosphere to which the sensor is exposed and therefore the value of the voltage across terminals 41 provides a direct measure of oxygen concentration. This voltage can either be directly measured or amplified as required. It should be understood that FIG. 6 is a very simplified view but it represents a typical, conventional circuit for use with gas sensors of this type.

It will be seen in FIG. 1 that gas entering the barrier 3 is forced by the disk 4 to pass with a lateral component through the disk 3 and exits from the lower portion of the barrier which is not covered by the polythene disk 4. The gas then enters the tape 5 through the annular region 9 and then reaches the sensing electrode catalyst 6.

An additional "diffuser" membrane (not shown in FIG. 1) of low diffusion resistance may optionally be placed between the PTFE backing tape 5 and the composite polythene disk 4 porous PTFE disk 3 to facilitate the spreading of the gas diffusion flux across the electrocatalyst section 6.

It has been found that by causing the gas to follow a longer path through the barrier 3 than would occur if it passed directly from the access hole 2 to the electrode catalyst 6, a smaller current can be more easily generated, thus prolonging the life of the metallic counter electrode. Furthermore, the arrangement enables bulk flow effects to be minimized and due to its simple construction as compared with previous sensors is relatively cheap to produce.

The disc 3 is described as the barrier, but the tape 5 could also act as a restriction although it should preferably have minimal effect in this connection providing it acts as a barrier against electrolyte flow.

Figure 2:
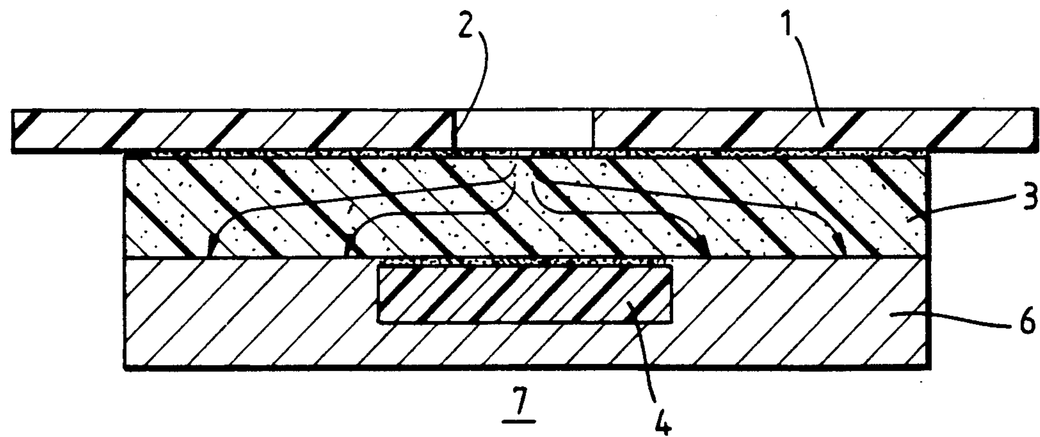
FIG. 2 is a longitudinal section through part of a second example.

FIG. 2 illustrates part of a sensor similar to that shown in FIG. 1 but in this case the porous PTFE disk 3 (19 mm diameter and 0.18 mm thickness) also acts as a backing tape in place of the tape 5 in the FIG. 1 example while the polythene disk 4 is embedded within the electrode catalyst layer 6.

In the FIG. 1 example, a number of heat sealing steps are required. It is essential, however, for the polythene disk 4 to be heat sealed to the PTFE disc 3 to ensure that the correct gas diffusion path is followed.

The FIG. 2 example is preferred since the number of heat sealing steps is reduced. Indeed, a single heat sealing tool can be applied just once to achieve the heat seal between the PTFE disc 3 and the plate 1 and between the polythene disc 4 and the disc 3. This latter arrangement is the most preferred since not only is a single heat sealing step necessary but it virtually eliminates free internal gas space and there will be no orientation effects due to relative movement between the component parts.

Figure 3:
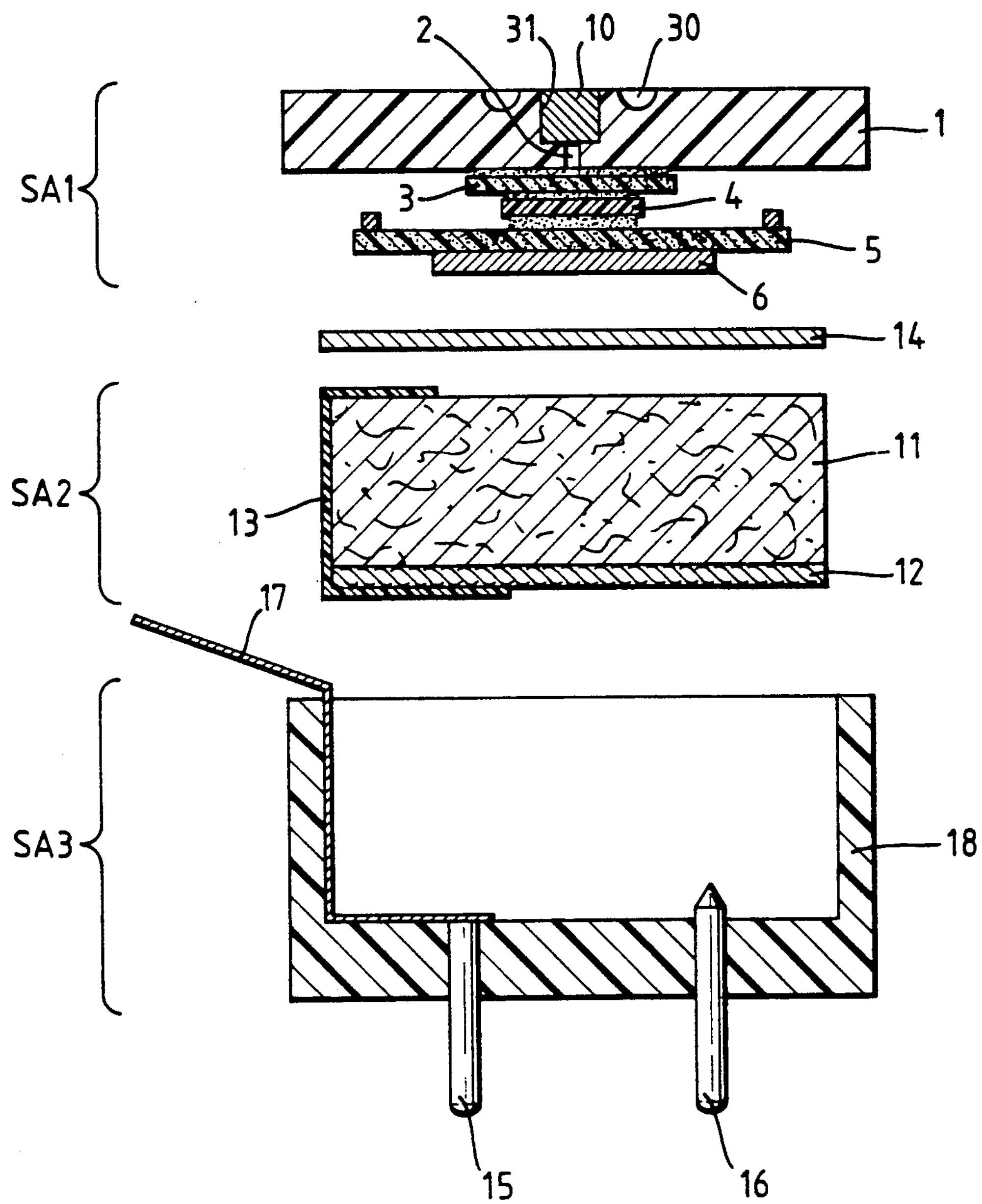
FIG. 3 is a partially exploded longitudinal section through a third example.

FIG. 3 illustrates a complete sensor in an exploded view which is not to scale based on the FIG. 1 example. In this example, the plate 1 is provided with an O-ring groove 30 to enable the sensor to be sealed to an enclosing housing while the gas access hole 2 communicates with a counterbore 31 in which is inserted a porous VYON plug 10 which acts to exclude water droplets.

The components 1-10 form a first sub-assembly SA1. A second sub-assembly SA2 comprises a pre-formed porous Pb wool anode 11 (counter electrode) with an expanded stainless steel mesh disk current collector 12 secured within a thin, insulating plastics clip 13. The sub-assemblies SA1 and SA2 are connected together with a separator 14 between them.

A third sub-assembly SA3 comprises an ABS can 18 having a cup-shaped form. A pair of Ni PCB pins 15, 16 extend through the base of the base plate 14 so as to contact the sensing electrode catalyst layer 6 and the anode 11 respectively. Connection between the pin 15 and the sensing electrode catalyst layer 6 is achieved via a Ni foil current collector 17.

The sensor is assembled by placing sub-assembly SA2 into sub-assembly SA3. The can 18 is then filled with electrolyte. Sub-assembly SA1 is then placed in the can 18 with separator 14 between sub-assemblies SA2 and SA1. The separator will wet up with the electrolyte.

It should be noted that although the invention has been described in connection with two electrode sensors, it is also possible for use with three electrode sensors in which a reference electrode is also provided. Furthermore, although the sensor is particularly suitable for use with oxygen, it could be used with any other gas which reacts electrochemically at the sensing electrode. With gases which react anodically at the sensing electrode, such as carbon monoxide, hydrogen sulphide, etc, the metallic counter electrode needs to be replaced with a suitable electrode able to undergo an electrochemical reduction (cathodic) reaction.

Figure 4:
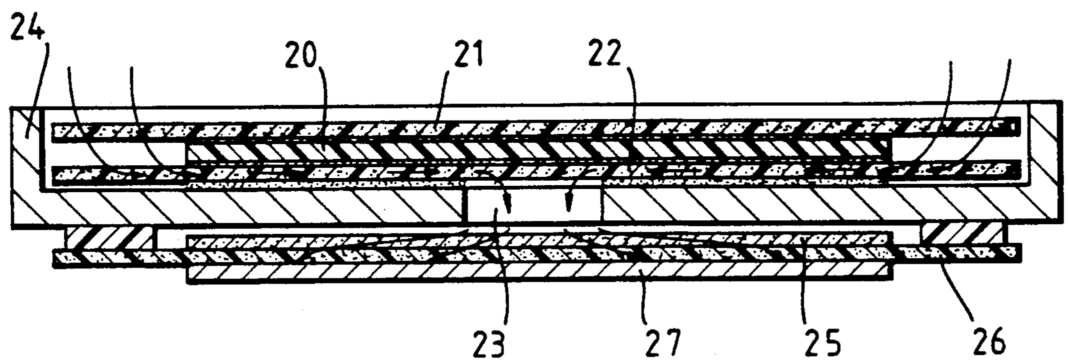
FIG. 4 is a longitudinal section through part of a fourth example.

FIG. 4 illustrates a further example of a gas sensor. A polythene disc 20 (12 mm diameter and 0.10 mm thickness) is sandwiched between two porous PTFE discs 21, 22 (19 mm diameter and 0.18 mm thickness) with the contacting surfaces being (heat) sealed between polythene and PTFE as shown dotted in the diagram.

Gas enters from the periphery of the discs 21, 22 and is forced to diffuse transversely (laterally) along the disc 22 which constitutes the main (gas phase) diffusion barrier, thence through an orifice 23 (which is non-restrictive having a 2 mm diameter and 3 mm length) formed in a sensor body 24. The sandwich of disc 20 and discs 21, 22 is sealed into the sensor body 24, the sealed areas being shown dotted.

Gas passing through the orifice 23 passes through a diffuser 25 (12 mm diameter and 0.18 mm thickness) which is optional, a porous PTFE backing tape 26 (19 mm diameter and 0.8 mm thickness) and into an electrocatalyst layer 27 (12 mm diameter and 0.18 mm thickness) where it undergoes an electro-chemical reaction.

The unit shown in FIG. 4 can be formed as a sub-assembly and the different components can be heat sealed together as shown in a single heat sealing step by application of a heat seal shoe against the upper PTFE disc 21. The application of this shoe can be done in a controlled manner so as to cause the polythene disc 20 partially to impregnate the pores of the discs 21, 22 so as to affect the diffusion resistance of the discs. In addition, or alternatively the heat sealing can be arranged to cause the pores of the discs 21, 22 to be partially closed thus increasing the diffusion resistance.

The sub-assembly shown in FIG. 4 can be incorporated into a full gas sensor of the type shown in FIG. 3 in place of the sub-assembly in SA1 shown in that diagram.

Figure 5:
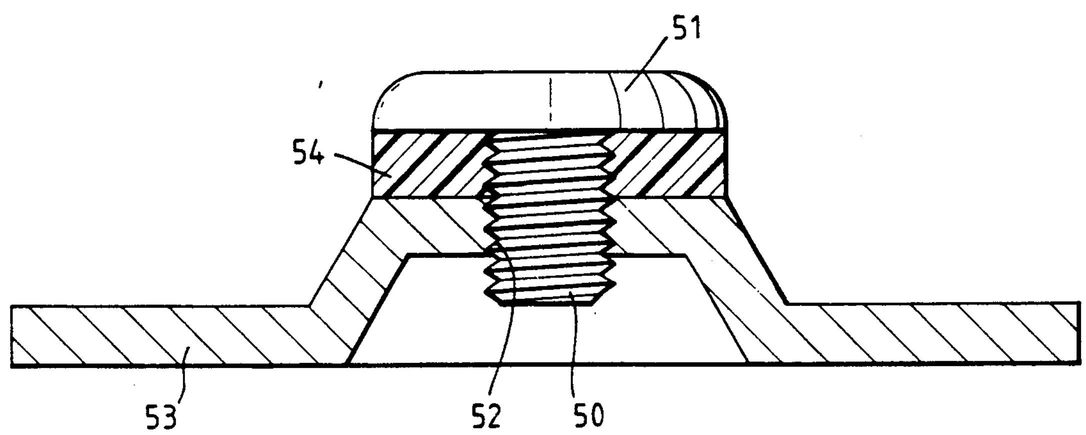
FIG. 5 is a longitudinal section through part of a fifth example.

FIG. 5 illustrates a further example in which a screw 50 having a wide flange 51 is screw-threaded into a bore 52 in a metal cap 53. A PTFE washer 54 is sandwiched between the flange 51 and the cap 53. In practice, gas diffuses laterally inwards towards the shank of the screw 50 through the PTFE washer 54 and then percolates through the bore 52 via the screw-threads. One of the significant advantages of this construction is that the diffusibility can be relatively easily controlled simply by turning the screw 50 and adjusting the compression of the washer 54.

We claim:

1. A gas sensor comprising a gas sensing device and a gas diffusion control assembly for controlling the rate of access of gas or vapor to the sensing device, the assembly comprising a gas inlet defining an axis; a restriction to the rate of flow of gas or vapor from said gas inlet in the form of a porous diffusion barrier extending across said gas inlet transverse to said axis to control bulk flow of gas therethrough; and control means for causing all gas or vapor passing out of said inlet into said diffusion barrier to diffuse through part of said barrier along a path with a lateral outward component relative to said axis, whereby said barrier also limits the flow rate of gas by diffusion therethrough, and wherein said porous diffusion barrier constitutes the sole barrier between said gas inlet and said sensing device for limiting bulk flow and for achieving diffusion control.

2. A sensor according to claim 1, wherein said sensing device comprises an electrochemical sensor for the measurement of concentrations of gas or vapor in accordance with the limiting current principle, said sensing device comprising an electrolytic cell having a sensing electrode, a counter electrode and an intervening body of electrolyte.

3. A gas sensor comprising a sensing electrode catalyst layer; a counter-electrode; and a gas diffusion control assembly comprising a gas inlet defining an axis; a restriction to the rate of flow of gas or vapor from said gas inlet in the form of a porous diffusion barrier extending across said gas inlet transverse to said axis to control bulk flow of gas therethrough; and control means for causing all gas or vapor passing out of said inlet into said diffusion barrier to diffuse through part of said barrier along a path with a lateral outward component relative to said axis, and wherein the porous diffusion barrier is fixed directly to the sensing electrode catalyst layer, whereby said barrier also limits the flow rate of gas by diffusion therethrough, and wherein the porous diffusion barrier constitutes the sole barrier between said gas inlet and said sensing electrode catalyst layer for limiting bulk flow and for achieving diffusion control.

4. A sensor according to claim 3, wherein said porous barrier and said control means act as both said diffusion barrier and a sensing electrode support.

5. A gas sensor comprising a first sub-assembly including a gas sensing electrode; a gas inlet defining an axis and forming part of a gas path to said gas sensing electrode; a restriction to the rate of access of gas or vapor to said gas sensing electrode in the form of a porous diffusion barrier transverse to said axis to control bulk flow of gas therethrough; and means for causing all gas or vapor to diffuse through part of said barrier along a path with a lateral component relative to said axis; a second sub-assembly including a counter electrode; and, a third sub-assembly to which said first and second sub-assemblies are mounted, said third sub-assembly including electrical contacts connected to the gas sensing and counter electrodes respectively, whereby said barrier also limits the flow rate of gas by diffusion therethrough, and wherein the porous diffusion barrier constitutes the sole barrier between said gas inlet and said gas sensing electrode for limiting bulk flow and for achieving diffusion control.

6. A sensor according to claim 5, wherein said restriction restricts the rate of flow of gas or vapor from said gas inlet.

7. A sensor according to claim 5, wherein said restriction restricts the rate of access of gas or vapor to said gas inlet.

* * * * *